United States Patent [19]

Hauser et al.

[11] Patent Number: 5,282,838
[45] Date of Patent: Feb. 1, 1994

[54] DUAL CHAMBER CARDIAC PACEMAKER EMPLOYING HYSTERESIS TO MAXIMIZE THE NUMBER OF NORMALLY CONDUCTED VENTRICULAR BEATS WITH AN OPTIMUM A-V DELAY FOR PACED VENTRICULAR BEATS

[75] Inventors: Robert G. Hauser, Long Lake; Julio C. Spinelli, Shoreview, both of Minn.

[73] Assignee: Cardiac Pacemakers, Inc., St. Paul, Minn.

[21] Appl. No.: 894,872

[22] Filed: Jun. 8, 1992

[51] Int. Cl.[5] ............................................. A61N 1/362
[52] U.S. Cl. ............................................. 607/9; 607/30
[58] Field of Search ................................. 128/419 PG

[56] References Cited

U.S. PATENT DOCUMENTS

| | | | |
|---|---|---|---|
| 4,421,116 | 12/1983 | Markowitz | 128/419 PG |
| 4,554,921 | 11/1985 | Boute et al. | 128/419 PG |
| 4,856,524 | 8/1989 | Baker, Jr. | 128/419 PG |
| 5,016,630 | 5/1991 | Moberg | 128/419 PG |
| 5,024,222 | 6/1991 | Thacker | 128/419 PG |

Primary Examiner—William E. Kamm
Assistant Examiner—Scott M. Getzow
Attorney, Agent, or Firm—Haugen and Nikolai

[57] ABSTRACT

A DDD pacemaker including stimulating means to stimulate the ventricles of a heart after a predetermined A-V delay period includes means for adjusting the A-V delay period to enhance the probability of detecting naturally occurring ventricular depolarization signals when such signals are being detected at a predetermined rate and switching to a more hemodynamically appropriate A-V delay period when paced beats predominate. The invention is implemented in software run on a microprogrammable controller comprising the DDD pacemaker.

15 Claims, 2 Drawing Sheets

DUAL CHAMBER CARDIAC PACEMAKER EMPLOYING HYSTERESIS TO MAXIMIZE THE NUMBER OF NORMALLY CONDUCTED VENTRICULAR BEATS WITH AN OPTIMUM A-V DELAY FOR PACED VENTRICULAR BEATS

BACKGROUND OF THE INVENTION

I. Field of the Invention:

This invention relates generally to the design of cardiac pacemakers, and more particularly to a dual-chamber A-V sequential pacemaker having the capability of automatically adjusting the A-V delay based upon the presence or absence of normally conducted ventricular beats whereby the A-V delay for stimulated beats and the number of normal ventricular beats occurring during intermittent pacing can be optimized.

II. Discussion of the Prior Art:

As is explained in the introductory portion of the Markowitz U.S. Pat. No. 4,421,116, dual chamber pacemakers incorporate means for both stimulating and sensing in both the atrium and ventricle of the heart. The pacemaker is coupled to the heart, via a pacing lead through which sensed atrial and ventricular depolarization signals can pass to the pacemaker circuitry and through which stimulating pulses may be delivered to either or both of the atrium and ventricle. With a dual chamber pacing system, there are four possible modes of pacing as follows:

i. Intrinsic activity sensed in both the atrium and ventricle—no pacing.

ii. Intrinsic activity sensed in atrium and not in ventricle—pace the ventricle.

iii. No intrinsic activity sensed in the atrium and ventricle depolarization sensed—pace the atrium.

iv. No intrinsic activity sensed in either the atrium or ventricle—pace both atrium and ventricle.

A problem exists when a physician attempts to set the A-V delay of the pacemaker because that optimum delay is dependent upon the particular pacing mode in progress. This is attributable to the fact that the propagation time is different for an electrical stimulus to move from the right atrium to the left atrium if a paced beat is involved rather than a normally conducted beat originating at the sinus node. Similarly, it is found to take a greater time for an electrical stimulus to propagate from the right ventricle, i.e., the paced ventricle, to the left ventricle during ventricular pacing than occurs when a normally conducted beat is involved which travels from the A-V node through the bundle of Hiss and the Purkinje fibers. This abnormal deactivation sequence will impair the efficacy of the ventricular contraction. To avoid this situation from occurring, in patients with intrinsic conduction, a long A-V delay, i.e., longer than the P-R interval, would be indicated, to allow the R wave to inhibit the pacemaker. Nevertheless, if a higher degree block develops over time and it becomes necessary to pace the ventricles, a shorter A-V delay would be indicated to optimize the atrial contribution to the ventricular volume.

It is the principal object of the present invention to provide a dual chamber pacer in which the optimum A-V delay is set for paced ventricular beats and still maximizing the probability of sensing intrinsic ventricular contractions before issuing a pacing spike when the pacemaker is operating in one or the other of the atrial synchronous mode or the atrial-ventricular sequential mode, i.e., modes ii and iv, above. A DDD pacemaker is said to be operating in the atrial synchronous mode when the patient's heart has a spontaneous or naturally occurring atrial depolarization at the appropriate time in the heart beat cycle and which is sensed by the atrial sense amplifier in the pacemaker which initiates a time delay, following which a ventricular stimulation pulse will be delivered if no spontaneous ventricular beat is detected. In the atrial-ventricular sequential mode, a spontaneous atrial depolarization (P-wave) does not take place within the appropriate time interval from a preceding ventricular depolarization in accordance with a selected minimum heart rate. In that event, an atrial stimulation pulse is delivered and timing circuitry within the pacemaker establishes an atrial-ventricular time delay interval. Following its completion, ventricular stimulation pulse is delivered unless a spontaneous ventricular depolarization is detected during that interval.

In prior art programmable pacemakers, the A-V delay interval along with various other operating parameters of the pacemaker may be physician selected or programmed by means of an external programming device. Once programmed, the A-V delay interval may be different for atrial synchronous and atrial-ventricular sequential pacing modes. However, this A-V delay is the same whether the patient has normal auriculo-ventricular conduction.

The most efficient ventricular contraction occurs when the atrial stimulus is normally conducted to the ventricles. The restoration of A-V synchrony by artificial pacing in patient's suffering from heart block improves cardiac function and true A-V synchrony. In patients with sick sinus syndrome and/or intermittent A-V block, it is desirable to allow for the normal depolarization of the ventricles whenever possible. This would require the programming of an A-V interval longer than the P-R interval (>150 ms), to allow the R-wave to inhibit the pacemaker. Nevertheless, during the periods where this normal conduction does not take place, it will be required to reduce the A-V delay to its optimum value for paced beats, normally around 150 ms. Thus, naturally occurring beats are preferred. Moreover, the intrinsic conduction also saves battery life. For these reasons, the programming of a long A-V delay seems appropriate to maximize the probability of detecting normally conducted ventricular beats and thereby inhibiting the pacemaker from delivering a pacing pulse. This artificial lengthening of the A-V delay has the unfortunate result that if the patient goes into A-V block, the pacemaker will be pacing with a longer than optimum A-V delay, thereby worsening hemodynamic performance. The programmed A-V delay in a pacemaker has two completely different functions, depending upon whether the patient has been paced in the ventricles or if a normally conducted ventricular beat has been sensed. In the first case, the programmed A-V delay is determining the contribution of the atrial contraction to the ventricular filling, and it should be adjusted in such a way as to maximize the left atrial contribution. In the second case, its function is completely different. Here, it is determining how long the pacemaker should wait before issuing a ventricular pacing spike after a valid atrial event has occurred. As should be obvious to those skilled in the art, a conflict occurs between the two criteria that should be used to establish the A-V delay. Waiting longer than normal to allow for a normally conducted ventricular depolarization to occur will not allow pacing soon enough to compensate for the slowness of the abnormal pathways that the paced depolarization will use to propagate.

SUMMARY OF THE INVENTION

In accordance with the present invention, the DDD pacer includes a programmed microcontroller and it is programmed to execute an algorithm providing for two programmable A-V delays, namely, a long A-V delay (LAV) during which a search is made for intrinsic activity in the ventricle and a short A-V delay (SAV) that will be used to set the optimum A-V delay for ventricular paced beats as determined by a cardiologist for the particular patient. The pacemaker will begin pacing with the LAV, and if a predetermined level of intrinsic activity is not sensed in a preprogrammed interval, the LAV delay will be automatically switched to the SAV delay in an effort to optimize cardiac output. Ventricular paced beats are then counted and if a programmed number of such beats is accumulated without detecting intrinsic activity, the algorithm switches the A-V delay back to LAV and a new search is started to see if the above-mentioned predetermined level of intrinsic activity now exists. If it does not exist, the A-V delay is switched back to SAV and a new cycle started. But if the ratio of the number of sensed beats to the number of paced beats exceeds a preprogrammed threshold (intrinsic activity), the A-V delay remains at the LAV value for as long as the mentioned ratio remains above the threshold. In this fashion, the algorithm serves to maximize the probability of intrinsic activity while providing a means to switch to an optimum A-V delay for paced beats when only a low level of intrinsic activity is present.

In executing the above algorithm, precipitous changes are involved in the length of the A-V delay period upon switching between LAV and SAV. In an alternative embodiment, the pacemaker's programmable controller is programmed in accordance with an algorithm which tends to eliminate a sudden shift in the A-V delay period. When the routine following the second algorithm is executed, it starts with a short A-V delay (SAV). The total number of sensed beats and paced beats is accumulated and when it is determined that this total exceeds a preprogrammed value, the ratio of sensed beats to paced beats is computed in terms of a percent. If the computed percentage is greater than a preprogrammed threshold, the A-V interval is changed to the LAV value. If it were determined that the ratio of sensed beats to paced beats did not exceed the preprogrammed threshold, the then existing SAV is increased by a predetermined increment of time. A test is then made to determine whether the thus incremented SAV value is greater than or equal to a pre-established LAV delay value. If it is, then the A-V value employed will be reset to the original pre-established SAV value where it would remain for a predetermined number of paced beats. If the A-V value had not, as yet, exceeded the pre-established maximum for it, it is again incremented.

It can be seen, then, that this algorithm causes the A-V delay of the pacer to move between the SAV when a predominance of paced beats are being sensed to the LAV value in small increments of time rather than precipitously. This has the beneficial effect of avoiding the sudden hemodynamic changes that may occur if the A-V delay is suddenly incremented from the SAV to the LAV. This change would be particularly significant if no normally conducted beats occur. Other possible implementations will be obvious to those skilled in the art.

DESCRIPTION OF THE PREFERRED EMBODIMENT

The pacemaker of the present invention can be implemented in either a DDD or a DDDR (rate responsive) demand-type cardiac pacemaker. Pacemakers of this type are inhibited from delivering stimulating pulses to myocardial tissue during periods of on-going intrinsic (naturally occurring) stimulation. Moreover, in the case of the DDDR pacemaker, a physiologic parameter is sensed by a suitable sensing circuit contained within the pacemaker and is used to adjust the rate at which stimulating pulses are delivered as a function of physiologic demand. The optimal physiologic state for effecting beating of the heart is one which maintains A-V synchrony. Because naturally occurring beats usually use pathways which optimize this synchrony, the present invention functions to maximize the probability of detecting normally conducted ventricular beats while still maintaining an optimum A-V delay for ventricular paced beats.

Figure 1:
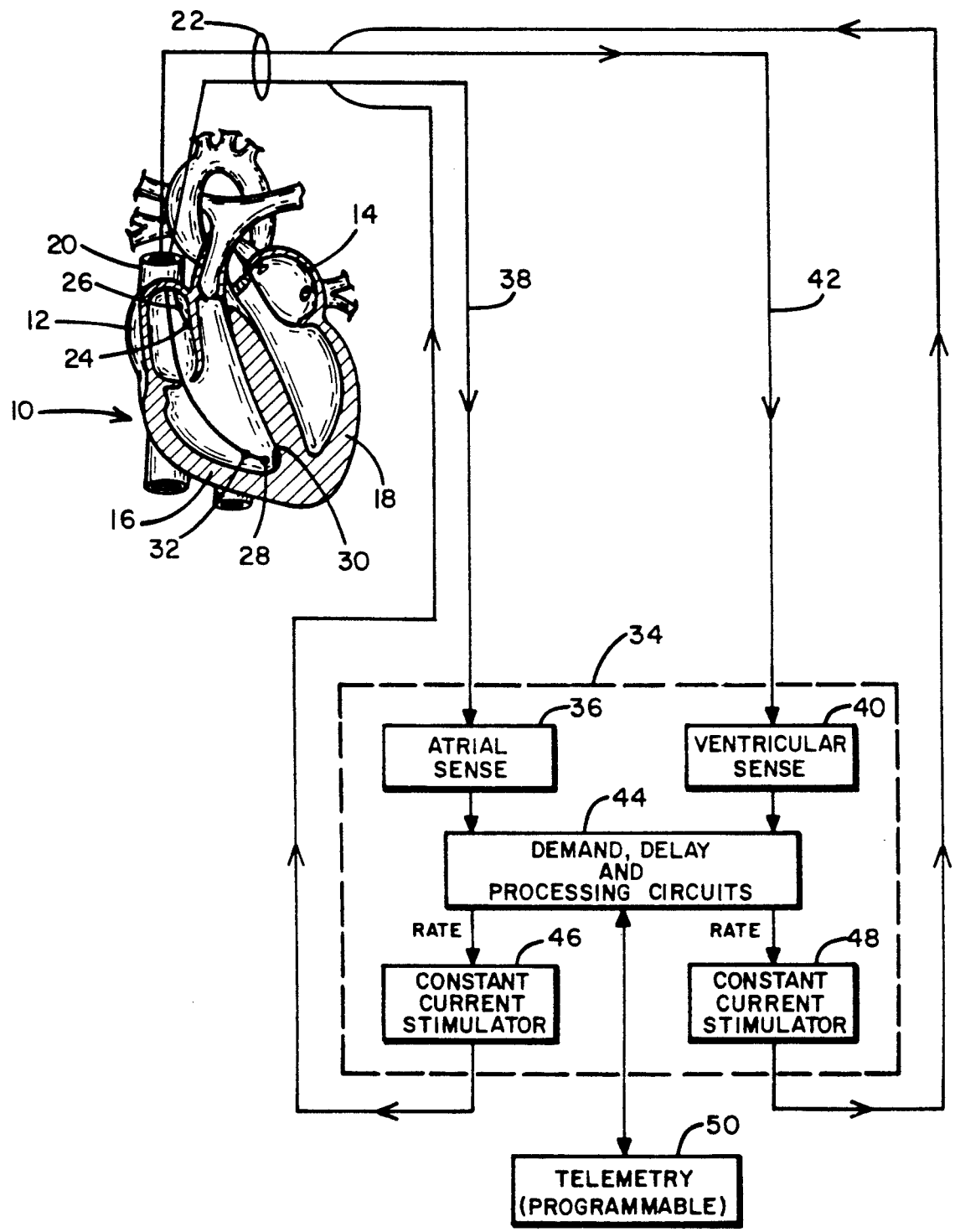
FIG. 1 is a functional block diagram of a DDD cardiac pacemaker in which the present invention may be implemented.

Referring to FIG. 1, there is shown a section view of a heart 10 having a right atrial chamber 12, a left atrial chamber 14, a right ventricular chamber 16 and a left ventricular chamber 18. Passing through the vascular system and the superior vena cava 20 is a pacing lead identified by numeral 22. This lead includes an atrial pacing electrode 24 which is positionable within the right atrium and an atrial sensing electrode 26 also contained in that chamber. The lead assembly 22 further includes a ventricular stimulating or pacing electrode 28 disposed at the apex of the right ventricle identified by numeral 30. A sensing electrode 32 is also mounted on this lead and is locatable within the right ventricle.

The lead 22 contains plural conductors joining these electrodes to terminals which are adapted to be coupled to a dual chamber pacer shown enclosed by the broken line box 34. The pacer includes atrial sensing circuitry 36 which is coupled by a conductor 38 in the lead 22 to the atrial sense electrode 26. Likewise, a ventricular sensing circuit 40 is connected by a conductor 42 passing through the lead 22 to the sensing electrode 32. The atrial sense circuit 36 and the ventricular sense circuit 40 provide inputs to a microcontroller-based electronics module 44 which controls the delivery of atrial and ventricular stimulating pulses to the electrodes 24 and 28, via pulse generators 46 and 58, respectively. As indicated in FIG. 1, various registers and memory modules within the demand, delay and processing circuitry 44 can be programmed, via transcutaneous signal transmissions, by means of a telemetry unit 50. Likewise, the telemetry unit 50 may be used to read out information from the implanted pacemaker 34.

While the present invention may be embodied in several prior art DDD or DDDR pacemakers, it is readily adaptable to the VIGOR Model 1230/35 manufactured and sold by Cardiac Pacemakers, Inc., applicant's assignee. The VIGOR 1230/35 contains a microprocessor and associated memory whereby a high degree of programmability is afforded. As it relates to the present invention, it permits the A-V delay interval between the occurrence of an atrial event and a ventricular paced pulse to be dynamically set. The algorithm of the present invention takes advantage of that capability, as will become more apparent as the description of the invention continues.

Figure 2:
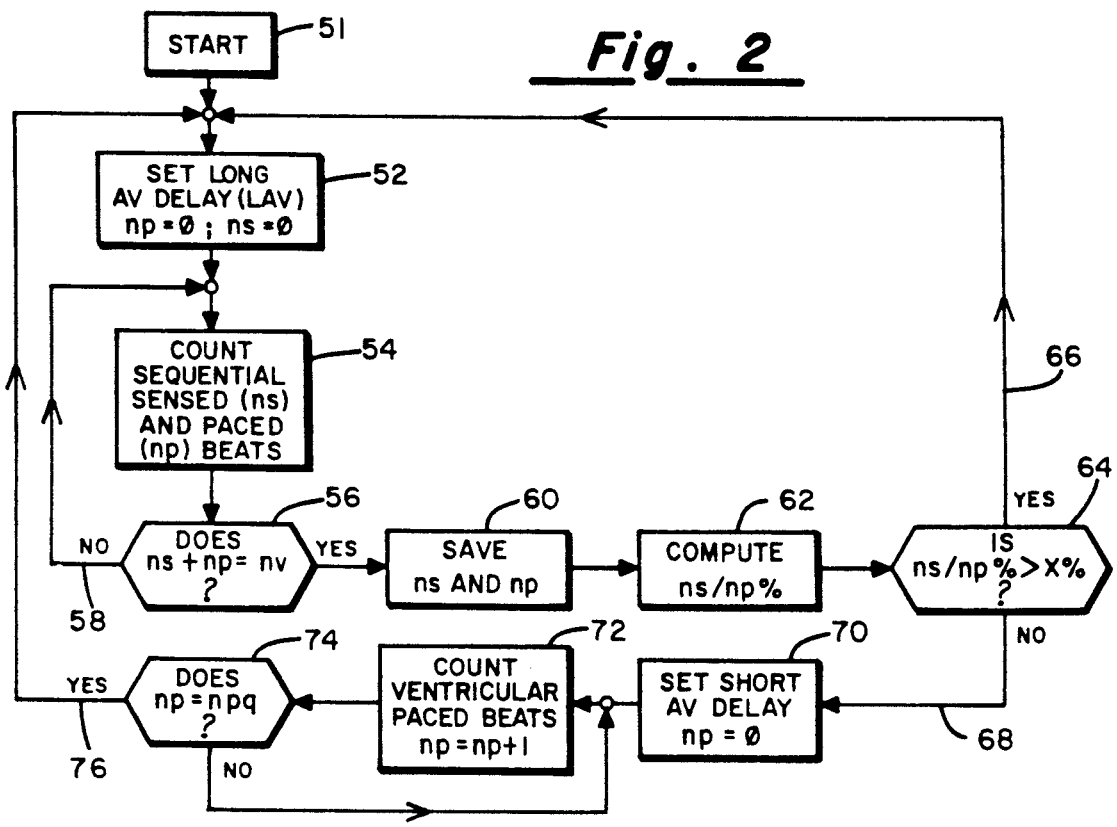
FIG. 2 is a software flow diagram showing the sequence of steps involved in implementing the A-V delay hysteresis concept of the present invention.

FIG. 2 is a software flow diagram illustrating the manner in which the digital programmable pacemaker can be operated to enhance the probability of detecting normal ventricular beats while at the same time establishing an optimum (usually shorter) A-V delay from a hemodynamic standpoint when natural beats are not occurring during the pacer's escape interval and the pacer is providing ventricular stimulating signals to the heart. Generally, the algorithm establishes a predetermined time interval and determines the ratio of the number of sensed beats to the number of paced beats. If this ratio exceeds a preprogrammed value, indicative that sensed beats are occurring at an acceptable frequency, the A-V delay remains at a long value. On the other hand, if the ratio of sensed beats to paced beats becomes less than the preprogrammed value, indicating that normally conducted beats are not being received at an acceptable rate, a short A-V delay period is established. After a predetermined number of ventricular paced beats have been counted, the A-V delay is again extended to its long value and the same program is again executed on an iterative basis.

With reference to FIG. 2, upon implantation and powering up of the pacemaker, a long A-V delay value, say 250 milliseconds, is set in a timing register while counters used to accumulate a count of paced beats and sensed beats are each set to zero (block 52). Counts of the number of sequential sensed beats ($n_s$) and paced beats ($n_p$) are tallied in separate counters (block 54). A test is continually made to determine whether the total of sensed beats and paced beats exceeds a predetermined count value $n_v$ which is programmed in and effectively constitutes the number of beats at the long A-V value to look for intrinsic activity, i.e., normally conducted beats (block 56). If the predetermined, programmed count value $n_v$ is not exceeded, control loops around via path 58 such that the counting of sensed and paced beats continues until the total exceeds $n_v$. When it does, the count values $n_s$ and $n_p$ are stored (block 60). Following that, the ratio of the number of sensed beats to the number of paced beats is computed and converted to a percentage value (block 62). This percentage ratio is compared to a preprogrammed value, X%, and if the percentage ratio exceeds that value, indicating that sensed beats are being detected on a somewhat regular basis, control follows path 66 back to the input of block 52 such that the long A-V delay remains active and the count values are cleared in anticipation of again executing the steps reflected by logic blocks 54, 56, 60, 62 and 64. The value of X may range from 50% to 100% depending upon the particular abnormality of the patient which the pacemaker is addressing. For example, if the patient suffers from left bundle branch block so that only a relatively few sensed beats are expected, X might be set at 90% to favor the short A-V delay associated with paced beats.

When it is determined at decision block 64 that the ratio of sensed beats to paced beats is less than the preprogrammed value, X%, indicating that paced beats are occurring relatively frequently, control follows path 68 to block 70 and the short A-V delay value, which may be determined by the cardiologists as providing a optimum hemodynamic benefit in terms of cardiac output, is used to establish the pacemaker's escape interval. At this point, the counter storing the number of paced beats is cleared and the number of ventricular paced beats is accumulated (block 72) until the accumulated value is found to equal a preprogrammed count corresponding to the number of beats in which the short A-V delay is to remain operative before extending the A-V delay to its long value. This quantity is referred to as $n_{pq}$ in decision block 74. When ultimately the number of paced beats becomes equal to the $n_{pq}$ quantity, control passes over line 76 to the input of block 52 where the long A-V delay value is again called for and used in establishing the period between an atrial event and the time that a paced beat is delivered by the pacemaker, provided no intervening natural beat is detected.

Figure 3:
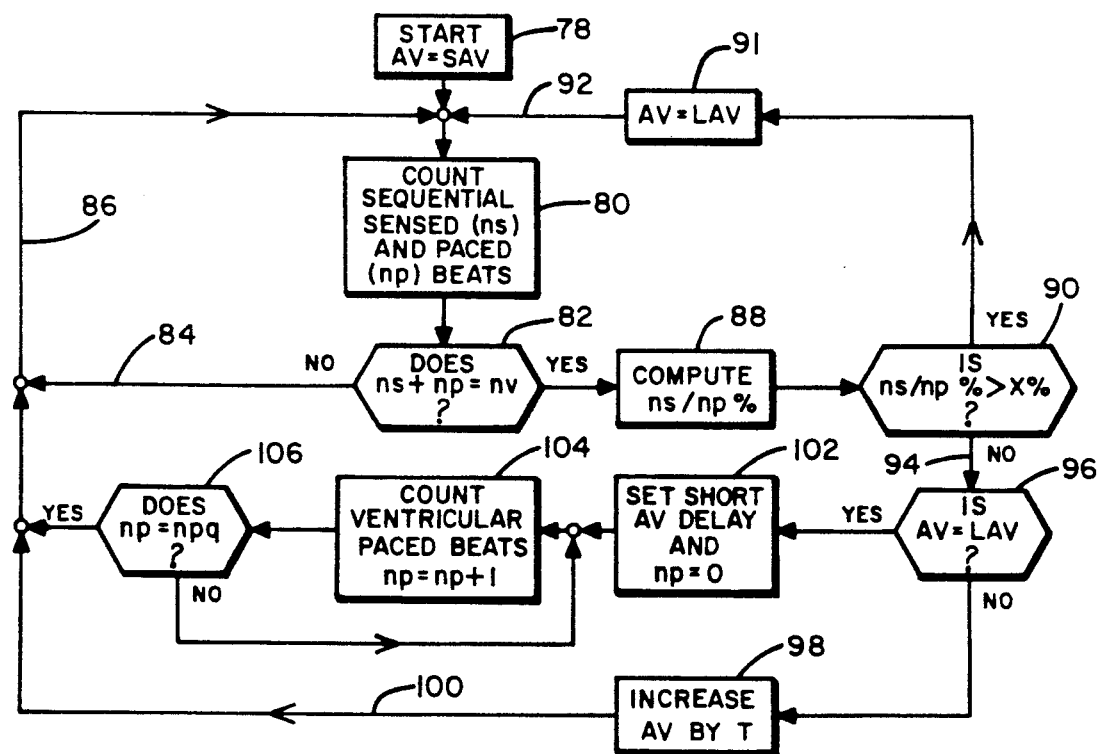
FIG. 3 is a second software flow diagram illustrating the sequence of steps for carrying out the invention in accordance with an alternative preferred embodiment.

Referring next to FIG. 3, there is shown by means of a software flow diagram an alternative algorithm for adjusting the A-V delay of a cardiac pacemaker in a way that maximizes the ability of the pacemaker to detect intrinsic heartbeat action while at the same time improving the hemodynamic performance of the heart when being paced by pulses emanating from the pacemaker. At start-up (block 78), counters are activated for separately tallying the number of sensed beats ($n_s$) and paced beats ($n_p$) (block 80). A test is made (block 82) to determine whether the total number of sensed beats and paced beats exceeds a preprogrammed count value ($n_v$). If not, control returns via path 84 and 86 to the input of block 80 until the count becomes equal to $n_v$. When this count has been reached, the microcontroller computes the percentage ratio of sensed beats to paced beats (block 88), and that percentage quantity is compared at block 90 to a preprogrammed percent number (X). If the ratio of sensed to paced beats exceeds X%, meaning that normal ventricular depolarizations are occurring at an adequate rate, the A-V delay interval involved is set in block 91 to the LAV. Control then passes, via path 92, to the input of block 80.

If the test at block 90 had indicated that the ratio of sensed beats to paced beats was lower than X%, control exits via path 94 and a second test is made at block 96 to determine whether the A-V delay interval then being used is equal to the preprogrammed LAV value. If it is determined that the then current A-V delay is not at its predetermined LAV, the current A-V delay is incremented by a time value, T, (block 98) with control returning, via path 100 and path 86, to the input of block 80. Each time control directs the flow through block 98, the then current A-V value of the pacemaker is incremented until ultimately, at block 96, the test will show that the current A-V value is equal to the preprogrammed maximum value LAV. When this occurs, the A-V delay interval for the pacer is reset to SAV (block 102). The paced ventricular beats are then counted until the total equals a preprogrammed count value $n_{pq}$ (blocks 104 and 106). When that predetermined number of paced beats has occurred, control again returns via path 86 to the input of block 80.

From what has been described, then, it is apparent that as long as there is a predominance of sensed beats being detected within an interval established by a predetermined count value, the A-V delay will remain constant at the LAV. However, should the ratio of sensed beats to paced beats fall below a pre-established threshold, before the A-V is set to LAV, the A-V delay value will be increased, in step-wise fashion, in an effort to allow ample time for sensed beats to occur during the pacer's escape interval. If the number of paced beats continues to predominate, causing the A-V interval to be ultimately increased to a predetermined maximum value (LAV), the A-V interval will be set to its short A-V (SAV) value for a predetermined number of paced beats, at which time it can again be increased in incremental steps.

In that the DDD pacemaker incorporating the present invention can be based upon a variety of microprogrammable controller chips, it is not deemed helpful or necessary to provide source code listings or object code listings for the program. Persons skilled in the art having the flow charts of FIGS. 2 and 3 available to them would be in a position to readily write the code for implementing the represented algorithms.

Although two exemplary embodiments of the present invention have been shown and described, it should be apparent to those of ordinary skill that a number of changes and modifications to the invention may be made without departing from the spirit and scope of the invention. For example, cardiac rhythm management devices are currently being developed which provide for bradycardia pacing, tachycardia conversion and defibrillation within a single implantable package. This invention can readily be adapted to such devices by following the present teachings. All such changes, modifications and alterations should therefore be recognized as falling within the scope of the present invention.

What is claimed is:

1. In a DDD pacemaker of the type including means for sensing natural and paced atrial depolarization signals, means for sensing natural and stimulated ventricular depolarization signals, atrial stimulating means, ventricular stimulating means and programmable microcontroller means coupled to said atrial and ventricular sensing means and said atrial and ventricular stimulating means for causing said ventricular stimulating means to issue a pacing pulse after a predetermined A-V delay period if a natural ventricular depolarization signal is not sensed within said A-V delay period, the improvement comprising:
    (a) means for establishing a first A-V delay value between the occurrence of one of a paced and natural atrial depolarization signal and the operation of said ventricular stimulating means when no natural ventricular depolarization signal intervenes, said first A-V delay value selected to be of a length sufficiently long to enhance the chance of detecting natural ventricular depolarization signals in said A-V delay period;
    (b) means for establishing a second A-V delay value between the occurrence of one of a paced and natural atrial depolarization signal and the operation of said ventricular stimulating means when no natural ventricular depolarization signal intervenes, said second A-V delay value being shorter than said first A-V delay value and of a length which improves the hemodynamic performance of the heart; and
    (c) means for automatically shifting said A-V delay period between said first and second delay values based upon the relative rate of occurrence of said natural ventricular depolarization signals and said pacing pulses issued from said ventricular stimulating means during a time interval in which a count of the total of sensed natural ventricular depolarization signals and pacing pulses exceeds a predetermined value.

2. In a DDD pacemaker of the type including means for sensing atrial depolarization signals, means for sensing ventricular depolarization signals, atrial stimulating means, ventricular stimulating means, and microcontroller means coupled to each said sensing means and each said stimulating means for causing said ventricular stimulating means to stimulate the ventricle after a predetermined A-V delay period if a natural ventricular depolarization signal is not sensed within said A-V delay period, the improvement comprising:
    (a) means for setting said A-V delay period to a first value;
    (b) means for setting said A-V delay period to a second value less than said first value;
    (c) means including said microcontroller means operative during the period that said A-V delay is at said first value for determining whether the ratio of natural ventricular depolarization signals to stimulated ventricular depolarization signals over a predetermined total number of ventricular depolarization signals exceeds a predetermined value and, if so, setting said A-V delay period to said second value; and
    (d) means operative during the period that said A-V delay period is at said second value for counting the number of stimulated ventricular depolarization signals and setting said A-V delay period back to said first value when that count equals a predetermined number.

3. The DDD pacemaker as in claim 2 wherein said pacemaker further includes telemetry means coupled to said microcontroller means.

4. The DDD pacemaker as in claim 3 wherein said first value and said second value are programmably set via said telemetry means.

5. The DDD pacemaker as in claim 3 wherein said value of said ratio is programmable via said telemetry means.

6. The DDD pacemaker as in claim 3 wherein said predetermined total number of ventricular depolarization signals is programmable via said telemetry means.

7. The DDD pacemaker as in claim 3 wherein said predetermined number of stimulated ventricular depolarization signals to be counted during the period that said A-V delay is at said second value is programmable via said telemetry means.

8. In a DDD pacemaker of the type including means for sensing natural and paced atrial depolarization signals, means for sensing natural and paced ventricular depolarization signals, atrial stimulating means, ventricular stimulating means, and programmable microcontroller means coupled to said atrial and ventricular sensing means and to said atrial and ventricular stimulating means for causing said ventricular stimulating means to issue a pacing pulse after an A-V delay period if a natural ventricular depolarization signal is not sensed within said A-V delay period, the improvement comprising:
    (a) means for counting sequentially occurring natural and paced ventricular depolarization signals;

(b) means responsive to said counting means for computing the ratio of the number of natural ventricular depolarization signals to paced ventricular depolarization signals occurring within a period corresponding to the time for said means for counting to reach a predetermined total;

(c) means for comparing said ratio to a predetermined programmed value; and (d) means responsive to the outcome of said comparison for repetitively increasing said A-V delay period by a predetermined time increment when said ratio is less than said predetermined programmed value and maintaining an existing A-V delay period when said ratio exceeds said predetermined programmed value.

9. The DDD pacemaker as in claim 8 and further including:

(a) means for detecting when the A-V delay period is incremented on iterative cycles to a point where said period equals a predetermined maximum A-V delay value; and (b) means responsive to said detecting means for resetting said A-V delay period to a predetermined base value and maintaining said A-V delay period at said predetermined base value until a predetermined number of said paced ventricular depolarization signals have occurred.

10. The DDD pacemaker as in claim 9 wherein said pacemaker further includes telemetry means coupled to said microcontroller means.

11. The DDD pacemaker as in claim 10 wherein said predetermined total is programmably set via said telemetry means.

12. The DDD pacemaker as in claim 10 wherein said predetermined programmed value is programmable via said telemetry means.

13. The DDD pacemaker as in claim 10 wherein the length of said predetermined time increment is programmable via said telemetry means.

14. The DDD pacemaker as in claim 10 wherein said predetermined maximum A-V delay value is programmable via said telemetry means.

15. The DDD pacemaker as in claim 10 wherein said predetermined base value and said predetermined number of said paced ventricular depolarization signals are each programmable via said telemetry means.

* * * * *